United States Patent [19]

Hedge

[11] 4,107,099

[45] Aug. 15, 1978

[54] BOROHYDRIDE EXCHANGE RESINS AND THEIR USES AS REDUCING AGENTS AND IN PREPARATION OF VOLATILE METAL HYDRIDES

[75] Inventor: Ramesh Subayya Hedge, Danvers, Mass.

[73] Assignee: Ventron Corporation, Beverly, Mass.

[21] Appl. No.: 767,243

[22] Filed: Feb. 10, 1977

[51] Int. Cl.$^2$ .................... C07C 29/14; C22B 43/00; C07C 97/00
[52] U.S. Cl. ................ 521/30; 260/567.6 M; 260/567.6 P; 562/862; 252/432; 423/23; 423/87; 423/99; 423/138; 423/289; 521/31; 521/32; 521/38; 526/24
[58] Field of Search .............. 260/2.1 E; 526/24

[56] References Cited

U.S. PATENT DOCUMENTS

| 2,723,245 | 11/1955 | Wheaton | 260/2.1 E |
|---|---|---|---|
| 4,025,467 | 5/1977 | Brock | 260/2.1 E |

FOREIGN PATENT DOCUMENTS 876,054  8/1961  United Kingdom.

OTHER PUBLICATIONS

Ion Exchange Resins, R. Kunin, John Wiley & Sons, pp. 60–63 (2nd ed.).

*Primary Examiner*—Joseph L. Schofer
*Assistant Examiner*—Peter F. Kulkosky
*Attorney, Agent, or Firm*—Stanley A. Marcus; Royal E. Bright

[57] ABSTRACT

Anion exchange resins containing borohydride counter ions display essentially the same chemical activity as solutions of sodium borohydride but have the added advantage that products treated therewith are not contaminated with sodium ions or borate ions. Thus, alcohols can now be freed of carbonyl components without thereby being contaminated with borate; metal ions, such as silver, can be reduced to the free element; metal ions of groups IV-A to VI-A can be converted to volatile metal hydrides; and transition metal ions can be converted to the boride. The anion exchange resin is prepared by treating a strong base anion exchanger with aqueous sodium borohydride or sodium cyanoborohydride. Regeneration of the borohydride form from the borate proceeds directly with aqueous sodium borohydride.

4 Claims, No Drawings

4,107,099

BOROHYDRIDE EXCHANGE RESINS AND THEIR USES AS REDUCING AGENTS AND IN PREPARATION OF VOLATILE METAL HYDRIDES

FIELD OF THE INVENTION

This invention relates to ion exchange resins containing borohydride counter ions and their uses. In one aspect, the invention relates to a composition of matter comprising an ion exchange resin containing cyanoborohydride counter ions. In another aspect the invention relates to a method of making an anion exchange resin containing borohydride counter ions. In one embodiment in this aspect, the invention relates to treatment of a halide-containing strong base ion exchange resin with an aqueous solution of a borohydride. In another aspect, the invention relates to soluble quaternized polyamines containing a borohydride ion. In another aspect, the invention relates to the use of borohydride containing ion exchange resins. In one embodiment of this aspect, the invention relates to reduction of metal ions to the free element by contact with an anion exchange resin containing adsorbed borohydride ions; in another embodiment of this aspect, the invention relates to preparation of volatile metal hydrides by reacting a metal ion of group IV-A, V-A or VI-A with an anion exchange resin containing borohydride counter ions; in another embodiment of this aspect, the invention relates to the manufacture of transition metal borides by treatment of a transition metal salt with an anion exchange resin containing borohydride counter ions. In yet another aspect, the invention relates to reducing various organic materials, such as aldehyde found in organic alcohols, without thereby contaminating the solution with by-product borate, by treating said organic material with an anion exchange resin containing borohydride counter ions.

DESCRIPTION OF THE PRIOR ART

British Pat. No. 876,034, published Aug. 30, 1961 teaches that when the hydroxide form of strongly basic anion exchange resins is treated with an aqueous solution of a borohydride, there is obtained an anion exchange resin containing adsorbed borohydride ions.

DESCRIPTION OF THE INVENTION

Sodium borohydride is employed as a reducing agent in a broad spectrum of applications. It effectively reduces aldehydes and ketones to the corresponding alcohol and is further capable of reducing Schiff bases, acid chlorides, peroxides, quaternary halides and many other less well known functional groups. The chemical species responsible for the reductive properties of sodium borohydride is the borohydride anion. In many applications it is advantageous to secure the reducing properties of the borohydride species without releasing sodium and borate into the system being treated. This is particularly applicable to purification of bulk organic chemicals. Anion exchange resins containing borohydride provide a practical means of achieving this situation. The borohydride anion, once exchanged onto the resin, functions as a reductant; when oxidized to borate, however, it remains attached to the matrix.

The anion exchange resins that are useful are those that are strongly basic, for example, the crosslinked quaternary ammonium polystyrene anion exchange resins of the homogeneous gel or macroreticular types are useful. Suitable resins include those sold under the trademark AMBERLITE and AMBERLYST by the Rohm & Haas Company, Philadelphia, PA. AMBERLITE IRA-900 and AMBERLYST A-26 have been successfully employed.

It should be noted that, although the prior art understood that it was necessary to use ion exchange resins in the form of the hydroxide, it has been found that it is unnecessary to convert to the hydroxide and that conversion from other forms, such as the halide, is accomplished directly from either an aqueous solution or an aqueous alkaline solution of borohydride. That the borohydride anion can be exchanged for an anion such as the chloride is considered to be surprising and wholly unexpected; this discovery, of course, eliminates a process step from the generation of the borohydride containing ion exchange resin. The borohydride solution is very simply brought into contact with the anion exchange resin. In one embodiment, the resin in granular form is packed into a column of glass or other suitable material and the borohydride solution is percolated through the column. While this is probably the simplest and most convenient method, other contact methods are equally effective, including simple stirring in a suitable vessel or other contact that will not adversely affect the physical structure of the beads. Room temperatures can be used, as desired.

Similarly, the cyanoborohydride anion can be exchanged onto the ion exchange resin simply by using a solution of a cyanoborohydride, such as sodium cyanoborohydride and passing it over the resin, which can be in either the hydroxide or chloride form.

While it is preferred to use aqueous solutions of borohydride to treat the anion exchange resin, conversion can also be effected in nonaqueous solvents which dissolve a borohydride, such as sodium borohydride or cyanoborohydride. Successful conversions have been done using diethylene glycol dimethylether. Other ethers and alcohols can be used.

Soluble anion exchange resins contemplated herein are those prepared by quaternizing a suitable liquid tertiary amine, followed by conversion of the quaternary ammonium salt to the borohydride, i.e., replacement of halogen with borohydride in a manner analogous to conversion of a conventional ion exchange resin.

Generally the aliphatic and aromatic amines can be quaternized: quaternary ammonium bases can also be used. Preferred are those that are readily soluble in water-immiscible organic solvents but insoluble in water. Borohydride can be substituted for the halide ion on these materials to produce a borohydride form liquid anion exchanger. Such materials permit application of borohydride reductions in non-aqueous systems and find utility in two-phase systems.

The soluble polyamines that are useful can contain a quaternary amine group either as part of a linear chain or as a pendant group. Reference is now had to the structure of the crosslinked strong base anion exchange resin, having a styrene divinylbenzene skeleton:

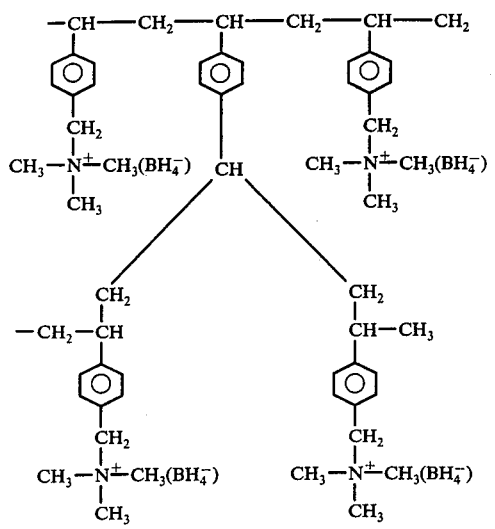

In the styrene divinylbenzene resin type, the quaternary amine group is pendant from the aromatic nuclei; the soluble amines contemplated can contain one or more quaternizable groups associated with or pendant from a backbone that is aliphatic, aromatic or mixed aliphatic/aromatic. A great number of suitable amines and ammonium bases is available and it is apparent, after considering the above, that these can readily be converted to the borohydride form using standard quaternization techniques followed by conversion of the salt to the borohydride according to the methods described herein.

Ammonium compounds that can be converted to the borohydride form and used as soluble ion exchangers are:

1. Trimethyl quaternary ammonium compounds of formula =

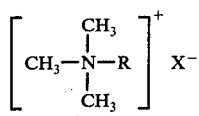

Where X is halide, such as chloride $R_1$ is an aliphatic group, such as alkyl or alkenyl of 4 to 22 carbon atoms or propylene alkyl ether where the alkyl group contains 4 to 18 carbon atoms or benzyl. Compounds within this general formula include:

Soya trimethyl ammonium chloride
Hydrogenated tallow trimethyl ammonium chloride
Palmityl trimethyl ammonium chloride
Coco trimethyl ammonium chloride
Tallow trimethyl ammonium chloride
Palmityl trimethyl ammonium chloride
Allyl trimethyl ammonium chloride
Benzyl trimethyl ammonium chloride,
as well as mixtures thereof.

2. Dimethyl quaternary ammonium compounds of formula =

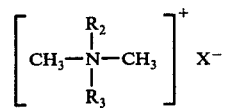

where X is halide, such as chloride $R_2$ and $R_3$ each independently is alkyl or alkenyl of 4 to 22 carbon atoms, propylene alkyl ether where the alkyl group contains 4 to 18 carbon atoms, or benzyl.

Compounds having this formula include:
Dialkyl ($C_{12}$–$C_{18}$) dimethyl ammonium chloride
Dialkyl ($C_{14}$–$C_{18}$) dimethyl ammonium chloride
Dialkyl ($C_{12}$–$C_{16}$) dimethyl ammonium chloride
Di hydrogenated-tallow dimethyl ammonium chloride
Dicoco dimethyl ammonium chloride
Distearyl dimethyl ammonium chloride
Dicoco dimethyl ammonium chloride (hexylene glycol)
Dimethyl alkyl ($C_{12}$–$C_{16}$) benzyl ammonium chloride
Dimethyl alkyl ($C_{10}$–$C_{18}$) benzyl ammonium chloride
Dimethyl stearyl benzyl ammonium chloride 3. Monomethyl quaternary ammonia compounds of formula

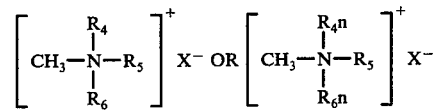

where
X is as defined
$R_4$, $R_5$ and $R_6$, each independently is alkyl or alkenyl of 4 to 22 carbon atoms, alkoxy of 2 to 7 carbon atoms in the alkyl group
n is an integer from 1 to 50 as desired to change solubility.

Representative compounds of this class include
Methyl tri ($C_8$–$C_{10}$) ammonium chloride
Methyl bis (2-hydroxyethyl) coco ammonium chloride
Methyl bis (polyhydroxyethyl) alkyl ammonium 4. Complex compounds containing more than one quaternary ammonium group:

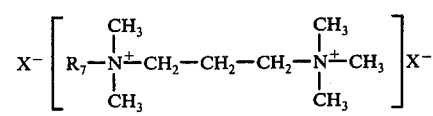

where
X is halide, such as chloride, methyl sulfate or ethyl sulfate
$R_7$ is alkyl or alkenyl of 4 to 22 carbon atoms.
Typical compounds include:
N-Tallow pentamethyl propane diammonium dichloride 5. Imidazolinium quaternary compounds of formula

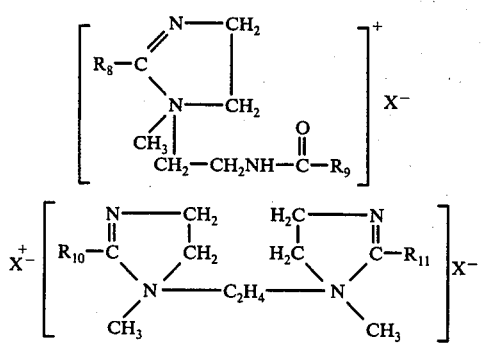

where
X is halide as defined or methyl or ethyl sulfate
$R_8$, $R_9$, $R_{10}$ and $R_{11}$ each independently is alkyl or alkenyl of 4 to 22 carbon atoms Typical compounds include:
Methyl-1-coco amido ethyl-2-coco imidazolinium methyl sulfate
Methyl-1-soya amideo ethyl-2-soya imidazolinium methyl sulfate
Methyl-1-tallow amido ethyl-2-tallow imidazolinium-methyl sulfate
Methyl-1-oleyl amido ethyl-2-oleyl imidazolinium-methyl sulfate
1-ethylene bis (2-tallow, 1-methyl, imidazolinium methyl sulfate)

Many of the above compounds are commercially available from Ashland Chemical Company, Columbus, Ohio.

Quaternary ammonium polymers useful herein are either commercially available or can be prepared as follows:

1. Commercially available polymers include
   A. Poly(dimethyldiallylammonium chloride) (Aldrich)
   B. Ionenes - Polyalkylene ammonium chlorides (Buckman Laboratories)
   C. Poly(vinylbenzyltrimethylammonium chloride) (Dow)
   D. Condensation polyamines — condensation products of polyalkylenepolyamines with dibasic acids, dialkylhalides or epichlorohydrin (Nalco, American Cyanamid, Hercules)
2. By quaternization of alkyleneamine polymers such as poly (ethyleneimine) available from Dow Chemical Co. or poly (propyleneimine) available from Interchemical Co.
3. By polymerization of a quaternary ammonium monomer such as methacryloyloxyethyl trimethylammonium methosulfate (Alcolac Chemical Co.)
4. By polymerization of an amino-containing monomer such as 4-vinyl pyridine (Reilly Chemical) or diethyl aminoethylacrylate (Union Carbide) followed by quaternization of the resulting polymer.

While the foregoing discussion and the following examples refer to the quaternary ammonium group, those skilled in the art will appreciate and understand that the phosphonium group and the sulfonium group will perform in a manner comparable to the ammonium group and that the phosphonium or sulfonium groups are freely interchangeable with ammonium.

EXAMPLE 1

A borohydride form anion exchange resin was prepared as follows: 50 grams of Amberlyst A-26 strong base chloride form anion exchange resin was packed into a 2 cm. glass column. 600 mls. of a 1% $NaBH_4$, 2.6% NaOH solution in water was passed through the resin over a period of 30 minutes. [Chloride was detected in the effluent indicative of exchange as opposed to physical adsorption of $NaBH_4$.] The resin was washed with distilled water until free of unexchanged $NaBH_4$ and NaOH.

The borohydride form resin was then analyzed for borohydride content by hydrogen evolution upon acidification. Analysis showed 1.2% hydrogen which translates to 3.97 meq. of borohydride per gram of dry resin. Boron analysis was 3.42% boron which corresponds to 4.2 meq. of boron per gram of dry resin. The theoretical exchange capacity of the resin is 4.2 meq./gram dry resin, hence essentially 100% exchange occurred.

Amberlyst A-26 is a quaternary ammonium type ion exchange resin having a macroreticular structure and is available from Rohm & Haas Co., Philadelphia, PA. Resins having a homogeneous gel structure are also available for use herein.

This experiment illustrates the proposition that a chloride-form strong base ion exchange resin can be directly converted to the borohydride form without conversion to the intermediate hydroxyl form. This aspect is considered to be surprising and wholly unexpected. It is further noted that there is virtually theoretical conversion from the chloride form to the borohydride form in alkaline medium; one would surely have expected the hydroxyl ions to compete with the borohydride ions, thereby reducing the efficiency of conversion.

EXAMPLE 2

A borohydride form anion exchange resin was prepared from an aqueous solution of sodium borohydride, as follows:

100 grams of chloride form Amberlyst A-26 anion exchange resin was slurry packed with water into a 7.5 cm. diameter glass column. 1000 ml. of a 4% $NaBH_4$ aqueous solution were passed through the resin over a period of a hours. The column effluent contained chloride ion. The resin was washed with distilled water until free of unexchanged $NaBH_4$.

After filtration the resin was analyzed for borohydride content by hydrogen evolution and total boron by titration. The resin contained 4.1 meq. of boron per gram of dry resin. Based on borohydride content, the conversion to borohydride form resin is 93% theoretical.

Here again, it is seen that direct conversion from chloride form to borohydride form proceeds with a surprising degree of efficiency.

EXAMPLE 3

A borohydride form anion exchange resin was prepared using an ion exchange resin having a homogeneous gel structure. 20 grams of chloride form Amberlite IRA-900 was slurry packed with water into 2 cm. diameter glass column. 175 mls. of a 0.7% $NaBH_4$, 2.3% NaOH aqueous solution were passed through the resin over a period of thirty minutes. The column effluent was found to contain chloride ion indicating exchange of the borohydride anion onto the resin. The resin was washed with distilled water until free of unexchanged $NaBH_4$ and caustic.

After filtration the resin was analyzed for borohydride content by hydrogen evolution and total boron by titration. The resin contained 1.20% hydrogen which corresponds to 3.7 meq. of $BH_4$ per gram dry resin and 3.3% boron corresponding to 3.8 meq. of boron per gram dry resin. Based on borohydride content the conversion to borohydride form resin is 97% of theoretical.

It has been found that almost theoretical conversion to the borohydride form is obtained using a dilute solution of sodium borohydride and sodium hydroxide. A solution of 12% $NaBH_4$ in 43% NaOH is commercially available from Ventron Corporation, Beverly, Mass., under the designation "SWS"; this solution provides a convenient form of borohydride and is diluted to provide the desired volume. While a threefold excess of borohydride over theoretical exchange capacity of the resin used will provide an almost 100% conversion, an equimolar amount of borohydride can be used, diluted to a volume of three times the volume of the resin bed on up to six times the bed volume.

EXAMPLE 4

A known weight of the resins (Amberlyst A-26 and Amberlite IRA-900) whose theoretical exchange capacity was known was slurry packed into a column. A solution of diluted SWS (SWS contains 43% NaOH and 12% $NaBH_4$; it is available from Ventron Corporation) containing borohydride equal to the exchange capacity of the resin was passed through the column bed. The volume of the solution was varied (three times bed volume and six times bed volume) while the contact time (30 minutes) and mole ratio (1:1) were kept constant. The six-times bed volume is seen to provide about a 6% increase in efficiency.

| Experimental Conditions | IRA-900 Theoretical Resin Capacity | Meq $BH_4$1 gram dry resin | Meq Boron/ gram dry resin |
|---|---|---|---|
| Mole Ratio = 1:1 Contact Time = 30 minutes Volume of the borohydride solution = 3 bed volume | 3.8 meq. | 3.2(84%) | 3.6(94%) |
| Mole Ratio = 1:1 Contact Time = 30 minutes Volume of the borohydride solution = 6 | 3.8 meq. | 3.66(96%) | 3.79(100%) |
| AMBERLYST A-26 | | | |
| Mole Ratio = 1:1 Contact Time = 30 minutes Volume of the borohydride solution = 3 bed volume | 4.4 meq. | 3.8(86%) | 4.1(93%) |

EXAMPLE 5

In order to spend borohydride form anion exchange resins, (i.e., convert $BH_4^-$ to $BO_2^-$), 40 grams of Amberlyst A-26 borohydride form anion exchange resin prepared as in Example 1 were placed in 200 mls. of a 50% by volume acetone in water mixture and allowed to stand overnight. The resin was filtered and found inactive when tested for borohydride. Regeneration was attempted using both aqueous borohydride and aqueous alkaline borohydride.

A. 20 grams of spent Amberlyst A-26 resin in the borate form were packed in a 2 cm. glass column. 60 ml. of a 5% $NaBH_4$, 16% NaOH (dilute SWS) solution in water were passed over the resin over a period of 2 hours. The resin was then washed with distilled water until free of excess $NaBH_4$ and NaOH.

B. Ten grams of deactivated resin were packed into a 2 cm. glass column. 30 ml. of a 5% aqueous $NaBH_4$ solution were passed over the resin over a period of 2 hours. The resin was then washed with distilled water until free of $NaBH_4$.

Both resins were filtered, air dried and subsequently analyzed for borohydride content by hydrogen evolution and boron content by boron titration. The resin regenerated with caustic-borohydride solution yielded a borohydride content of 4.2 meq. per gram dry resin and a boron content of 4.2 meq. per gram dry resin. This corresponds to 95% reconversion to borohydride form. The resin regenerated using aqueous $NaBH_4$ had a borohydride content of 4.1 meq. borohydride per gram dry resin and 4.2 meq. boron/gram dry resin, a reconversion to borohydride of 93% theoretical.

| Regenerant | Theoretical Capacity | $MEQBH_4$ Gram Dry Resin | MEQ Boron Gram Dry Resin |
|---|---|---|---|
| Dilute SWS solution | 4.4 meq/gm | 4.2 meq(95%) | 4.2 meq |
| Aqueous $NaBH_4$ Solution | 4.4 meq/gm | 4.1 meq(93%) | 4.2 meq |

C. The procedure above was repeated using Amberlite IRA-900 anion exchange resin; the results are summarized below:

| Regenerant | Theoretical Capacity | Meq. $BH_4$1 Gram Dry Resin | Meq. Boron Gram Dry Resin |
|---|---|---|---|
| Dilute SWS solution | 3.8 meq/gm | 3.5 meq(92%) | 3.9 meq |
| Aqueous $NaBH_4$ solution | 3.8 meq/gm | 3.25 meq(86.0%) | 3.8 meq |

It is thus seen that the borate form of the resin can be almost quantitively converted to the $BH_4^-$ form by direct exchange of the counter ions. The somewhat better regeneration seen with dilute SWS may be due to the presence of $OH^-$ and may suggest an initial exchange of $BO_2^-$ to $OH^-$ followed by exchange of $OH^-$ to $BH_4^-$ although this by no means clear.

The borohydride form of the anion exchange resins have poor stability stored in water; it has been found that these resins have acceptable stability (shelf life) stored at elevated pH (greater than 12) and semi wet.

EXAMPLE 6

This Example illustrates the preparation of cyanoborohydride form anion exchange resin. 200 grams of Amberlyst A-26 were slurried into a 7.5 cm. diameter column with distilled water. 1 liter of a 3% aqueous sodium cyanoborohydride solution was passed through the resin bed over a period of two hours. Initially the column effluent contained no cyanoborohydride, hence it was exchanged onto the resin. The resin was washed with distilled water until free of excess cyanoborohydride, then filtered.

Resulting cyanoborohydride form anion exchange resin was analyzed for cyanoborohydride content by hydrogen evolution and cyanide titration. By hydrogen evolution analysis, 3.39 meq. of cyanoborohydride was found per gram of dry resin. By cyanide analysis the resin contained 3.05 meq. cyanoborohydride per gram of resin. Based on cyanide content this represents a 70% theoretical conversion.

EXAMPLE 7

This Example illustrates the generation of volatile hydrides with ion exchange resin containing borohydride: A 25 ml. solution containing 500 ppb of Arsenic was stirred with 1 gm. of A-26 anion exchange resin in borohydride form. The reaction vessel was connected to an absorption tube filled with a solution to absorb the volatile hydride of arsenic (i.e., arsine, $AsH_3$). The absorption solution is made by dissolving 1 gm. of silver diethyldithiocarbamate (SDDC) in 200 mls. of pyridine. The change in color of the adsorbing solution indicated that the arsenic was converted to volatile arsine. This technique is useful in the analysis of low level of arsenic.

EXAMPLE 8

This Example illustrates the reduction of metals with borohydride substituted ion exchange resin:

A. Reduction of Silver 100 ml. of a silver salt solution containing 5000ppm of silver at a pH of 4.5 was stirred with 1 gm. of borohydride form Amberlyst A-26 anion exchange resin in a beaker for thirty minutes. The reduced silver powder and the resin were filtered from the solutions. An analysis of the filtrate showed 0.05ppm silver.

The above reduction was also carried out over a range of pH (4.5 - 8.5).

The reduction was efficient in the entire range of pH.

B. Reduction of Copper

A 100 ml. solution containing 500ppm of copper sulfate was stirred with one gram of borohydride form Amberlyst A-26 anion exchange resin for half an hour. The reduced copper along with the resin was filtered from the solution. The filtrate was analyzed for copper and contained less than 0.05ppm of copper.

C. Reduction of Cadmium

A 100 ml. solution containing 500ppm of cadmium nitrate was stirred with 1 gm. of Amberlyst A-26 anion exchange resin in borohydride form for thirty minutes. The reduced cadmium and resin were filtered and filtrate analyzed for cadmium and found to contain less than 0.05ppm cadmium.

It is seen from the above that borohydride form anion exchange resins are highly effective in the removal of metals from solutions over a broad range of pH; the metals are readily recovered. These resins are of value in treating process effluents and the like to remove heavy metals therein.

EXAMPLE 9

This Example illustrates the application of borohydride form anion exchange resin for silver recovery from used photographic fixer. 10 ml. aliquots of a spent photographic fixer solution containing 0.55% Ag were diluted to 100 ml. and adjusted to 5 different pH levels: 4.5, 5.5, 6.5, 7.5, and 8.5. One gram of borohydride form Amberlyst A-26 anion exchange resin was added to each sample. The samples were stirred and allowed to stand at 20 C for 30 minutes.

The precipitated silver powder and the resin were filtered. The filtrate was analyzed by atomic absorption spectroscopy and contains less than 0.05ppm of silver.

Here again it is seen that the borohydride form of anion exchange resin is extremely useful to recover metal values from process effluents.

EXAMPLE 10

This Example illustrates the reduction of nickel salt to nickel boride. One gm. of Amberlyst A-26 anion exchange resin in borohydride form was stirred in 100 ml. solution of 1% $NiCl_2 \cdot 6H_2O$ for less than 5 minutes. The nickel was precipitated as a black powder, much of which as a fine coating on the resin beads. The coating on the bead is very stable as it could not be removed even on strong ultrasonic agitation.

EXAMPLE 11

This Example illustrates the reduction of an organic carbonyl compound by borohydride form Amberlite IRA-900 anion exchange resin.

A. Reduction in Protic Media

A solution containing 0.141 mg. of salicylaldehyde per ml. of ethanol was prepared. To 25 ml. of this solution 2 grams of borohydride form Amberlite IRA-900 were added. The mixture was allowed to stand at room temperature with intermittant shaking. 3-microliter samples were withdrawn from the reaction mixture at various intervals for analysis by liquid chromatography with ultraviolet detection. Analysis of salicylaldehyde indicated a 94% reduction in a 8 minutes.

B. Reduction in Aprotic Media

A solution containing approximately 100 mg/ml of salicylaldehyde in hexane was prepared. 25 ml. of this solution was added to 2 grams of borohydride form Amberlite IRA-900. The mixture was allowed to stand at room temperature with intermittant shaking. 3-microliter samples were analyzed for aldehyde content by liquid chromatography with ultraviolet detection. In 15 minutes an 88% reduction of aldehyde peak height was observed.

Salicylaldehyde was selected because the reduction could be followed by liquid chromatography. The borohydride form anion exchange resins are active in both polar and non-polar solvents. The chloride form anion exchange resin produced no change in salicylaldehyde content. Boron analysis indicated that there was no contamination of either solution by release of boron from the resin. Results obtained using the borohydride form Amberlyst A-26 resin were comparable.

EXAMPLE 12

Crotonaldehyde is an undesirable impurity in synthetic ethanol and is difficult to remove by conventional means. While reduction of aldehydes and ketones with sodium borohydride is known, such reduction is accompanied by release of borate and sodium ions into the product being treated; the net result is that one contaminant is replaced by another. Borohydride form anion exchange resins were evaluated as a means for reducing crotonaldehyde in ethanol. Not only is the crotonaldehyde reduced, but no borate is released into the product.

Ethanol containing various concentrations of crotonaldehyde was passed through a column packed with ion exchange resins in borohydride form. The column effluent collected in aliquots and tested for aldehyde by ASTM Test Method D1363-67. ("Permanganate Time Test")

A. Purification of Ethanol Containing 500ppm Crotonaldehyde

Although the 500ppm is an unrealistically high concentration of crotonaldehyde, this experiment was performed to test effectiveness of the resin under extreme conditions. 10 grams of Amberlite IRA-900 and Amberlyst A-26 resins in $BH_4^-$ form (see example 1) were slurry packed into separate columns. 150 mls of ethanol containing 500 ppm of crotonaldehyde were passed through each column at a flow rate of 2 mls/min at ambient temperature (23° C). After discarding the void volume, 50 ml aliquots were collected. The first 50 ml aliquots were tested by Permanganate Color Test (ASTM D1363-67) as follows: test sample was taken in a Nessler tube and placed in a constant temperature bath (15° C). When the sample reaches the specified temperature, 2 mls of $KMnO_4$ solution (0.2gm/liter) were added and thoroughly mixed. The time taken for the decolorization of Permanganate color is measured.

The remaining solution was passed through the column for the second time and a 50 ml aliquot tested for Permanganate Time. The last 50 ml sample was passed through the column for the 3rd time and subsequently tested for Permanganate time.

A series of ethanol samples containing known amounts of crotonaldehyde were also tested for Permanganate color to obtain semi quantitative information.

Permanganate test for ethanol samples containing known amounts of crotonaldehyde.

| Sample Tested | Permanganate Time* |
|---|---|
| Ethanol with 1ppm aldehyde | 15 min |
| Ethanol with 2ppm aldehyde | 11 min |
| Ethanol with 4ppm aldehyde | 7 min 30 sec |
| Ethanol with 10ppm aldehyde | 4 min |
| Ethanol with 39ppm aldehyde | 30 sec |
| Ethanol with 500ppm aldehyde | 0 |

*Due to the nature of the test, specifically visual end point detection, the times should be considered no better than ± 1 minute.

Permanganate test of ethanol samples after $BH_4^-$ resin treatment.

| Material Tested | Permanganate Time* |
|---|---|
| Pure ethanol | 51 min |
| Ethanol + 500ppm aldehyde | 0 (instant color loss) |
| 1st pass over IRA-900 ($BH_4^-$) | 3 min 40 sec |
| 2nd pass over IRA-900 | 7 min 30 sec |
| 3rd pass over IRA-900 | 10 min 30 sec |
| 1st pass over A-26 ($BH_4^-$) | 3 min 55 sec |
| 2nd pass over A-26 | 9 min 10 sec |
| 3rd pass over A-26 | 14 min 52 sec |

*Due to the nature of the test, specifically visual end point detection, the times should be considered no better than ± 1 minute.

Using the above calibration, it is apparent that approximately 1 ppm crotonaldehyde remains in the original 500ppm solution after a 3rd circulation over the resin. It is also noted that one pass over the resin reduces the 500ppm to about 10ppm.

B. Purification of EtOH Containing 10ppm Crotonaldehyde

Five grams of Amberlite IRA-900 and Amberlyst A-26 were slurry packed into separate columns using pure EtOH as solvent. The calculated capacities of these columns were 17.9 and 22 millimoles of $BH_4^-$ respectively. 100 mls of a 10ppm crotonaldehyde in EtOH solution were passed over each column at a flow rate of 2 ml/min at ambient temperature (24° C). After discarding the void volumes, the 1st 50 ml fractions were collected and tested.

| Material Tested | Permanganate Time |
|---|---|
| 10ppm untreated | 4 min |
| 10ppm IRA-900 treated | 49 min |
| 10ppm A-26 treated | 58 min |

C. Purification of EtOH Containing 39 ppm Crotonaldehyde in EtOH. (Slightly Higher But Still Realistic Level)

100 mls of a 39ppm crotonaldehyde in EtOH solution were passed through the same columns used for the 10ppm reduction at a flow rate of 2 ml/min and ambient temperature (24° C). The first 50 ml fractions were collected and tested.

| Material Tested | Permanganate Time |
|---|---|
| 39ppm crotonaldehydr in EtOH | 30 sec |
| 39ppm IRA-900 treated | 44 min |
| 39ppm A-26 treated | 49 min |

D. Reduction of Crotonaldehyde in EtOH from a Distillation Column 500 ml of a 34ppm crotonaldehyde in EtOH solution was placed in a 1000ml distillation flask and connected to a distillation apparatus. The first 50 ml of distillate was collected untreated and tested for Permanganate time to determine if the distillation was purifying the ethanol. No significant change in permanganate time was found. The rest of the distillate was passed over a 5 gram resin bed having a capacity of 10.8 millimoles of $BH_4^-$. The temperature of the distillate was 26° C which was 5° C above ambient temperature. The following results were obtained:

| Material Tested | Permanganate Time |
|---|---|
| Untreated distilled 34ppm | 30 sec |
| 1st treated 50 ml aliquot | 35 min |
| 2nd treated 50 ml aliquot | 37 min |
| 3rd treated 50 ml aliquot | 37 min |
| 4th treated 50 ml aliquot | 39 min |

The addehyde or ketone or, if present, peroxide and metal ions, can be an impurity in a variety of organic materials. The borohydride form exchange resin is effective. Other organic materials include glycols, esters, epoxides, amines, amides and monomers such as styrene and vinyl chloride. The borohydride form resin is effective as a reducing agent without releasing sodium, borate or, obviously, borohydride ions as contaminants.

EXAMPLE 13

This example illustrates the preparation of soluble quaternary ammonium borohydride ion exchangers and their uses. It also illustrates the use of borohydride form ion exchange resins to exchange borohydride on a variety of materials.

A. 5 grams of Amberlyst A-26 resin in borohydride from (See Example 1) were added to a 35 ml. solution of 7 grams methyl tri($C_8$-$C_{10}$ alkyl) ammonium chloride (available from Ashland Chemical Co. as Adogen 464) in ethanol. The mixture was stirred for five minutes and filtered. A sample of filtrate, on acidification with conc. HCl effervesced vigorously, indicating the presence of borohydride; confirmation of borohydride was obtained by testing with iodine solution and observing decoloration.

B. 10 mil. of the filtrate obtained above were mixed with 10 ml. of ethanol containing about 15 mg. of salicylaldehyde. Reduction of this aldehyde was monitored by liquid chromatography. There was a 50% reduction in aldehyde content in less than five minutes.

EXAMPLE 14

This example illustrates the preparation of a soluble polymeric quaternary ammonium borohydride ion exchanger.

A. Approximately 10 g. of a 35% aqueous solution of Poly(dimethyldiallyl ammonium chloride), from Aldrich Chemical Co., was diluted to 100 ml. with water. 5 g. of Amberlyst A-26 borohydride form resin was added to the solution. The solution was filtered through a funnel packed with glass wool to remove the resin beads. The filtrate was tested for the presence of borohydride. This was done by adding a few drops of concentrated HCl to a sample of the filtrate. Vigorous evolution of gas indicated the presence of borohydride.

B. 5 mls. of above filterate was mixed with a 20 ml. solution of ethanol containing about 30 mg. of Salicylaldehyde. The reduction of Salicylaldehyde was monitored by liquid chromatography and showed 75% reduction in less than 5 minutes.

EXAMPLE 15

This example illustrates the use of the borohydride form ion exchange resin to reduce peroxides in an organic liquid.

A sample of commercial tetrahydrofuran (THF) was tested for the presence of peroxide by the iodide test method. The immediate appearance of an intense red-brown color indicated the presence of substantial peroxide.

A portion of this THF sample was passed through a 2 cm. column packed with 10 grams of Amberlyst A-26 resin in borohydride form (See Example 1). When the effluent from the column was again tested for peroxide, the red-brown color was significantly slower in forming and was far less intense indicating a reduction in the level of peroxide upon treatment with the borohydride form resin.

What is claimed is:
1. A method of making an anion exchange resin containing borohydride counter ions which comprises treating a halide form anion exchange resin with a solution containing a borohydride.
2. A method according to claim 1 in which the solution comprises water, a borohydride and an alkali metal hydroxide.
3. A method according to claim 1 in which the solution contains sodium borohydride.
4. A composition comprising an anion exchange resin containing cyanoborohydride counter ions.

* * * * *